United States Patent [19]

Regas et al.

[11] Patent Number: 4,685,471

[45] Date of Patent: Aug. 11, 1987

[54] METHOD AND APPARATUS FOR PREDICTING AND DETECTING THE ONSET OF OVULATION

[75] Inventors: Jennine Regas, Denver; Ranjit S. Fernando, Aurora, both of Colo.

[73] Assignee: Zetek, Inc., Aurora, Colo.

[21] Appl. No.: 713,866

[22] Filed: Mar. 20, 1985

Related U.S. Application Data

[63] Continuation-in-part of Ser. No. 649,844, Sep. 11, 1984, abandoned.

[51] Int. Cl.$^4$ .............................................. A61B 10/00
[52] U.S. Cl. ...................................... 128/734; 128/738
[58] Field of Search ................................. 128/734, 738

*Primary Examiner*—Edward M. Coven

*Attorney, Agent, or Firm*—Rosen, Dainow & Jacobs

[57] ABSTRACT

A method and apparatus for predicting ovulation in a human female subject. The onset of menstruation of the subject is noted. Daily determinations are made of the electrical resistivity of the subject's saliva, beginning not more than five days following beginning of menstruation. The onset of ovulation is determined as a function of a peak resistivity measurement following onset of menstruation, which peak is followed by a nadir and subsequent sharp increase in saliva electrical resistivity measurement. Vaginal resistivity measurements may be made to confirm ovulation. A probe is used for the resistivity measurement. A probe includes a head or body with exposed imbedded electrodes.

27 Claims, 20 Drawing Figures

Fig_1

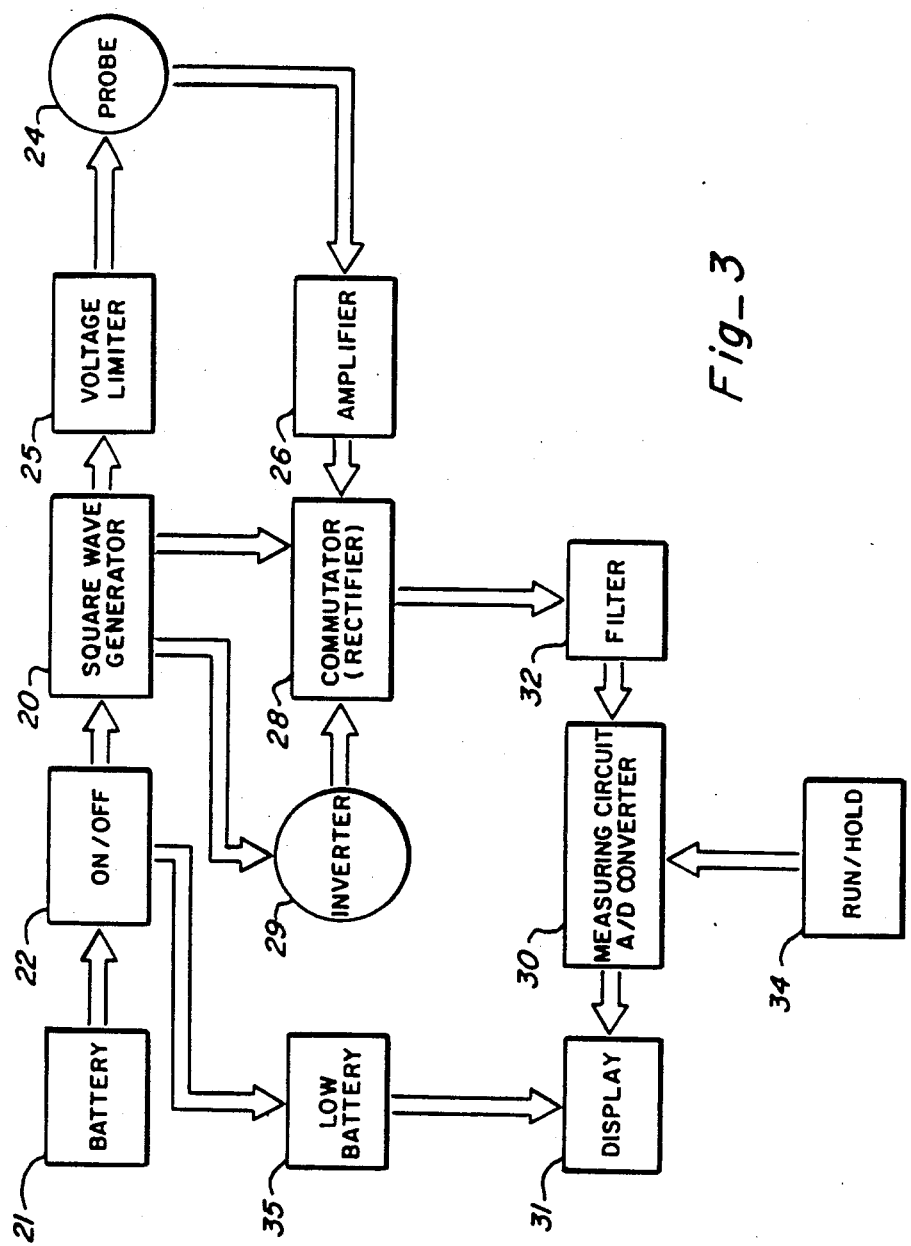
Fig_3

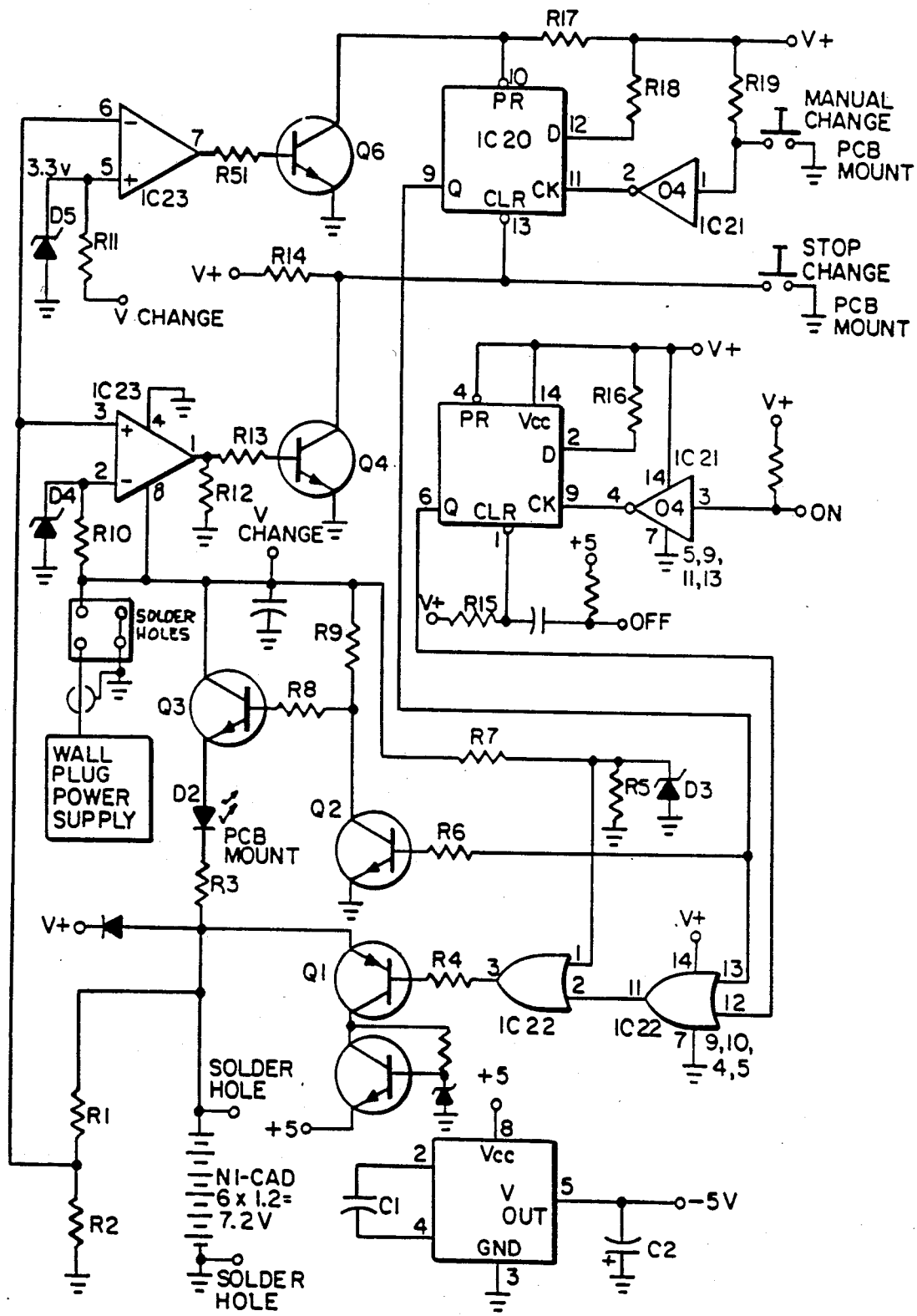
Fig_3A

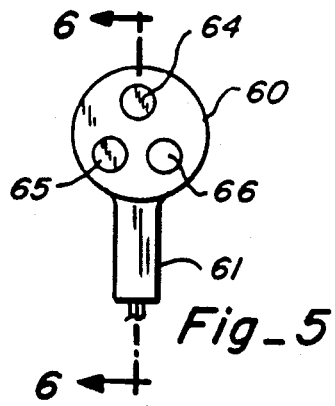
Fig_5
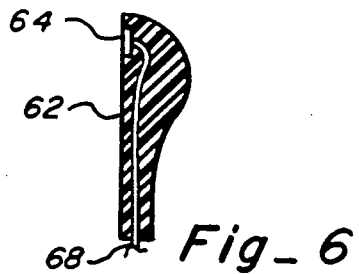
Fig_6
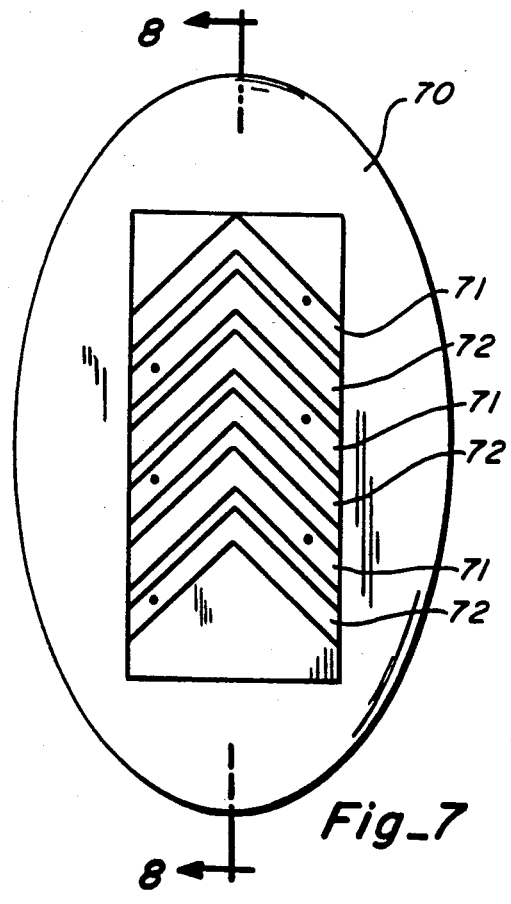
Fig_7
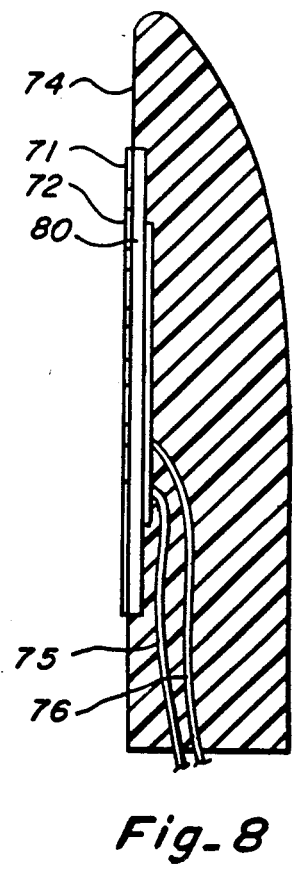
Fig_8

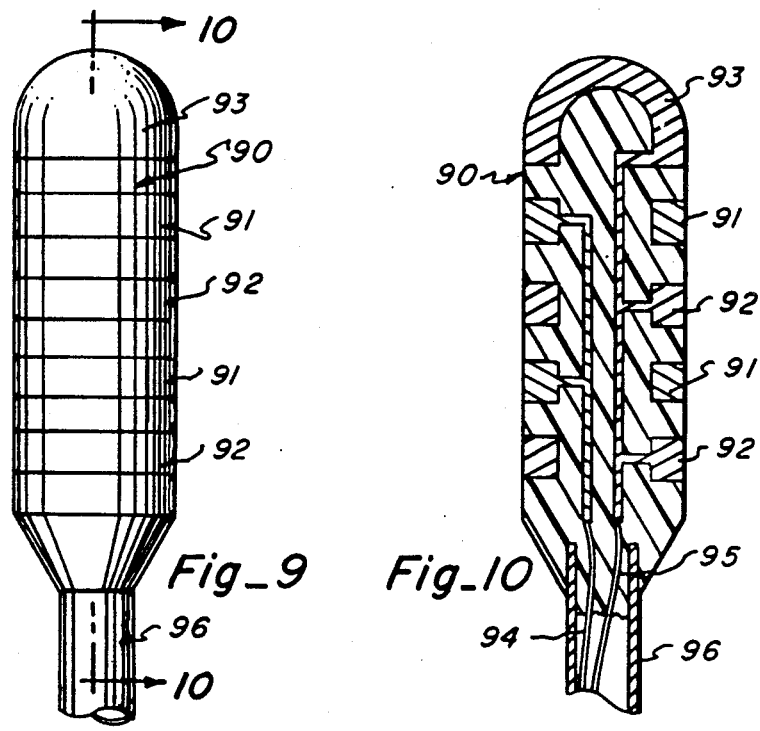
Fig_9  Fig_10
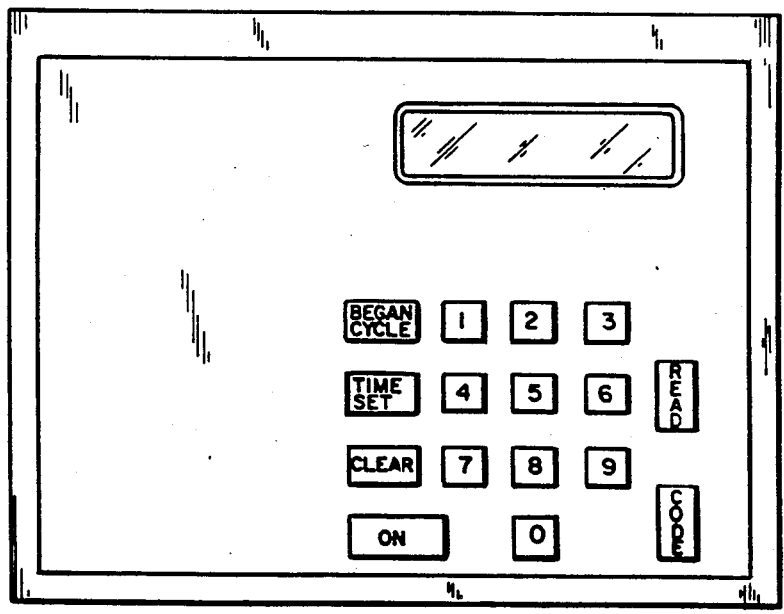
Fig_11

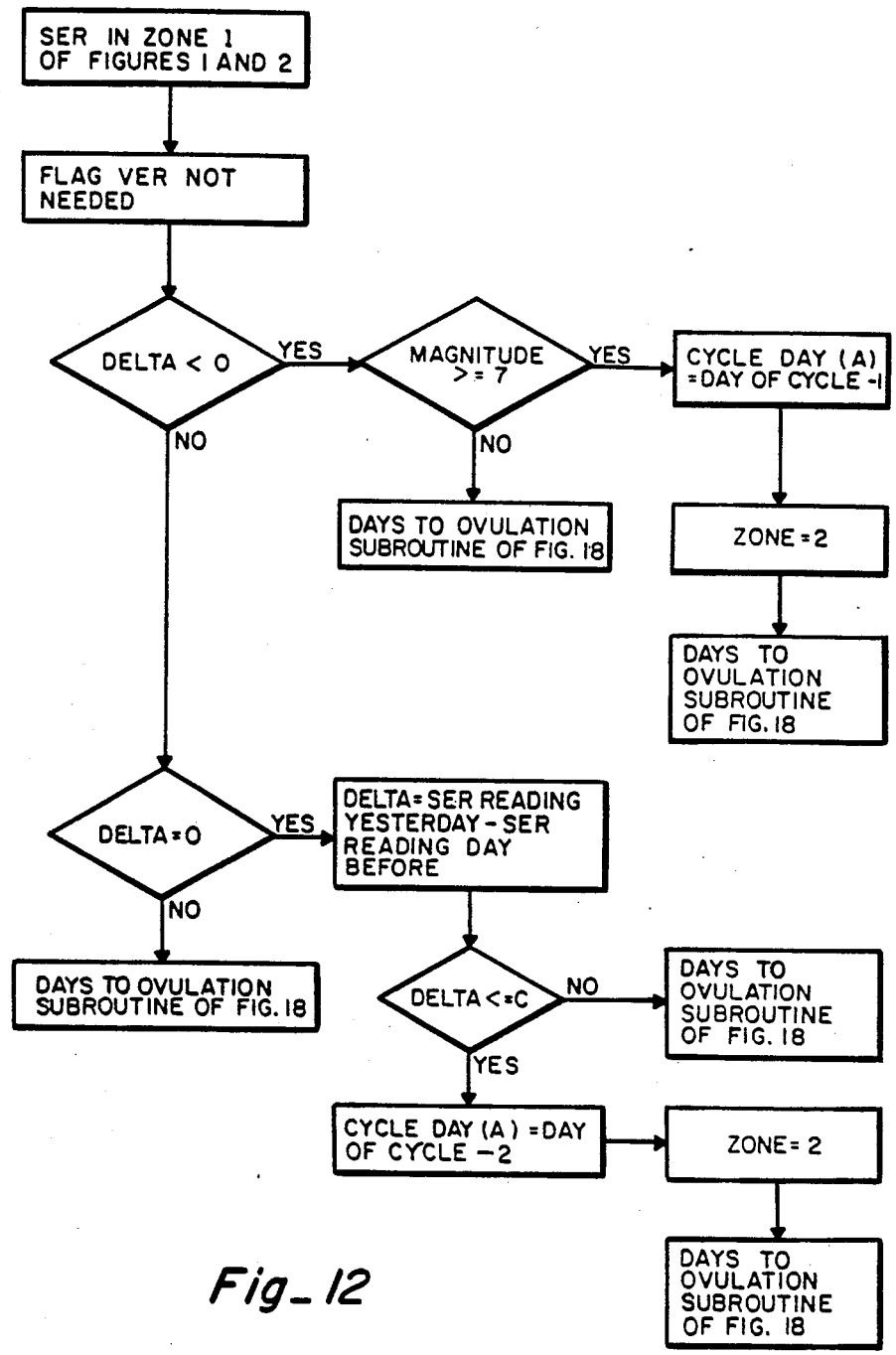
Fig_12

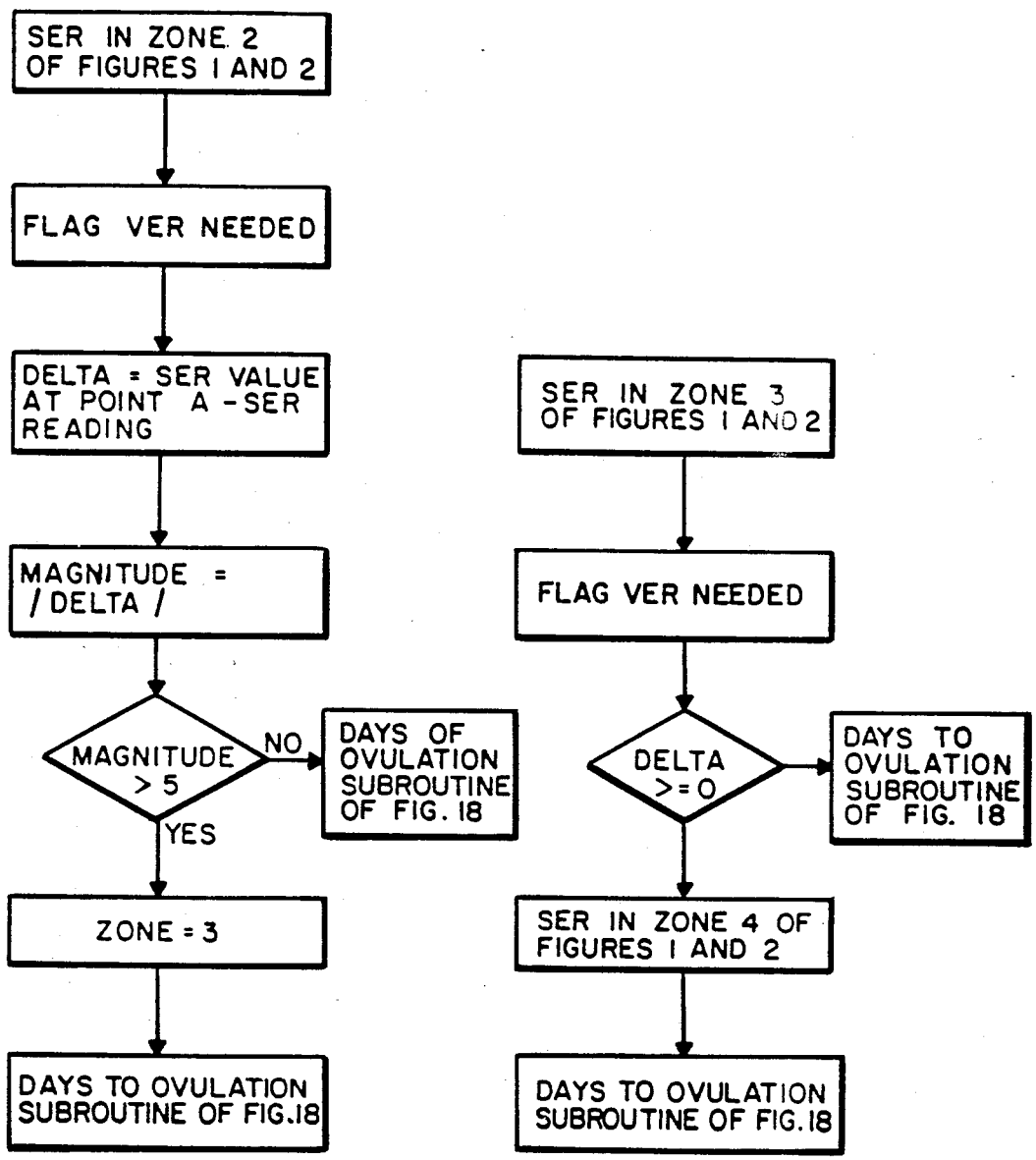
Fig_13    Fig_14

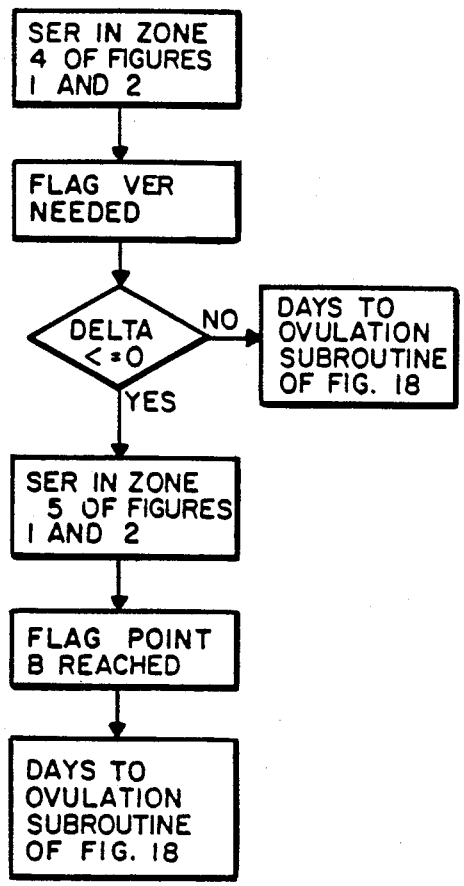
Fig_15
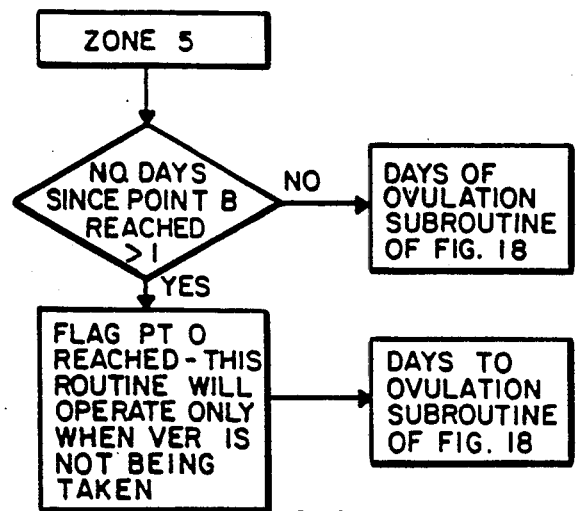
Fig_16
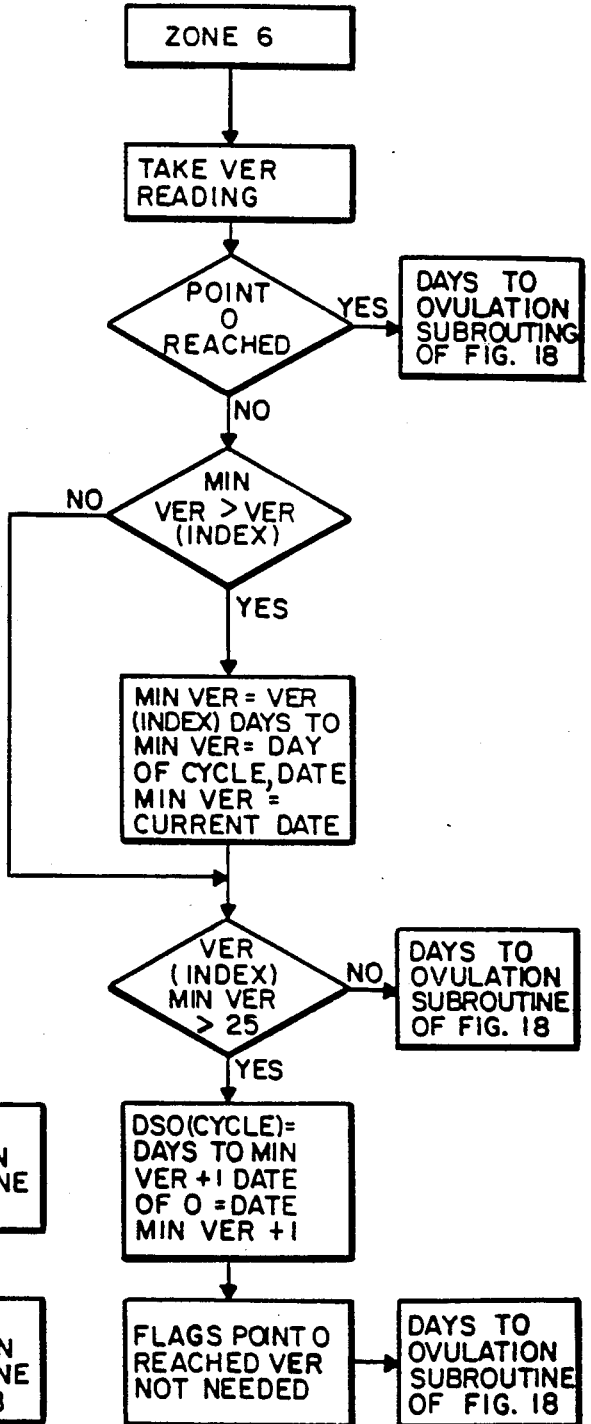
Fig_17

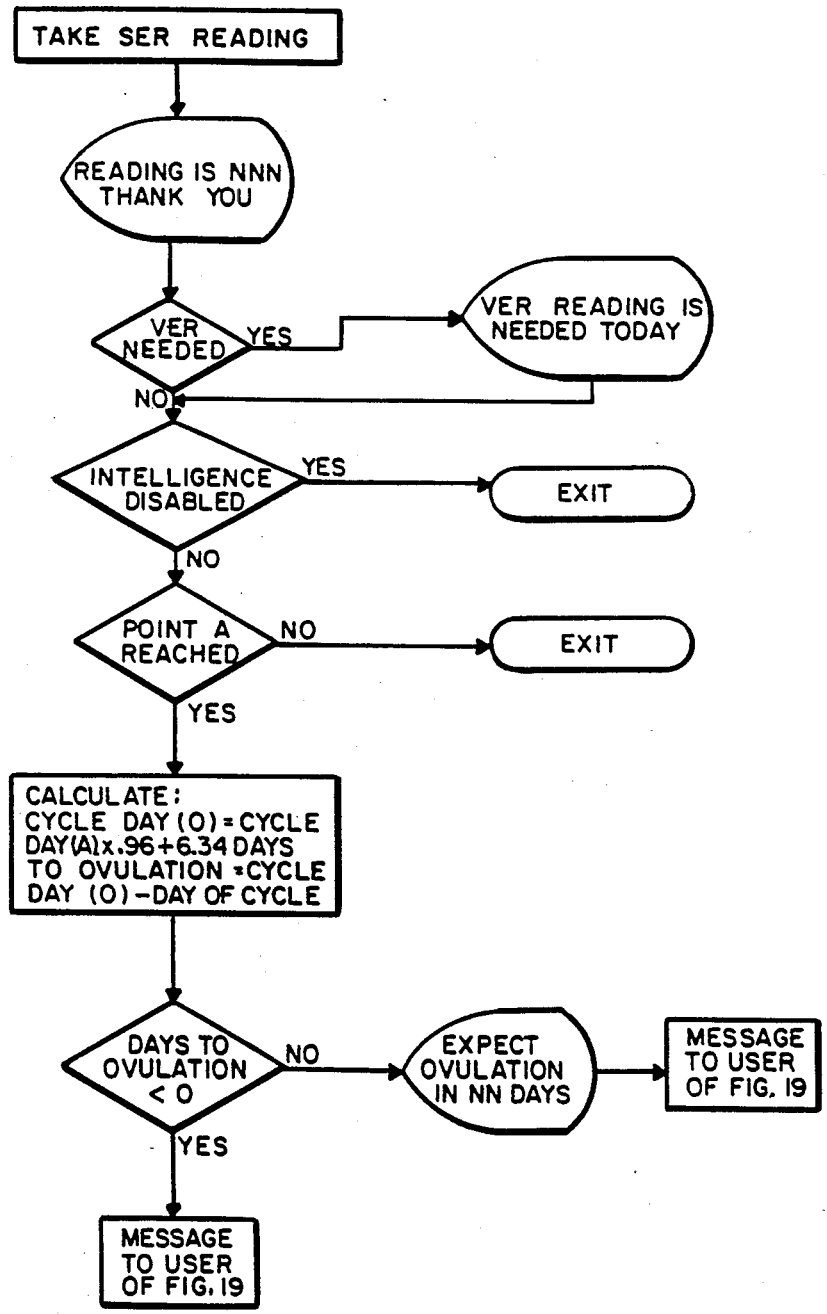
Fig_18

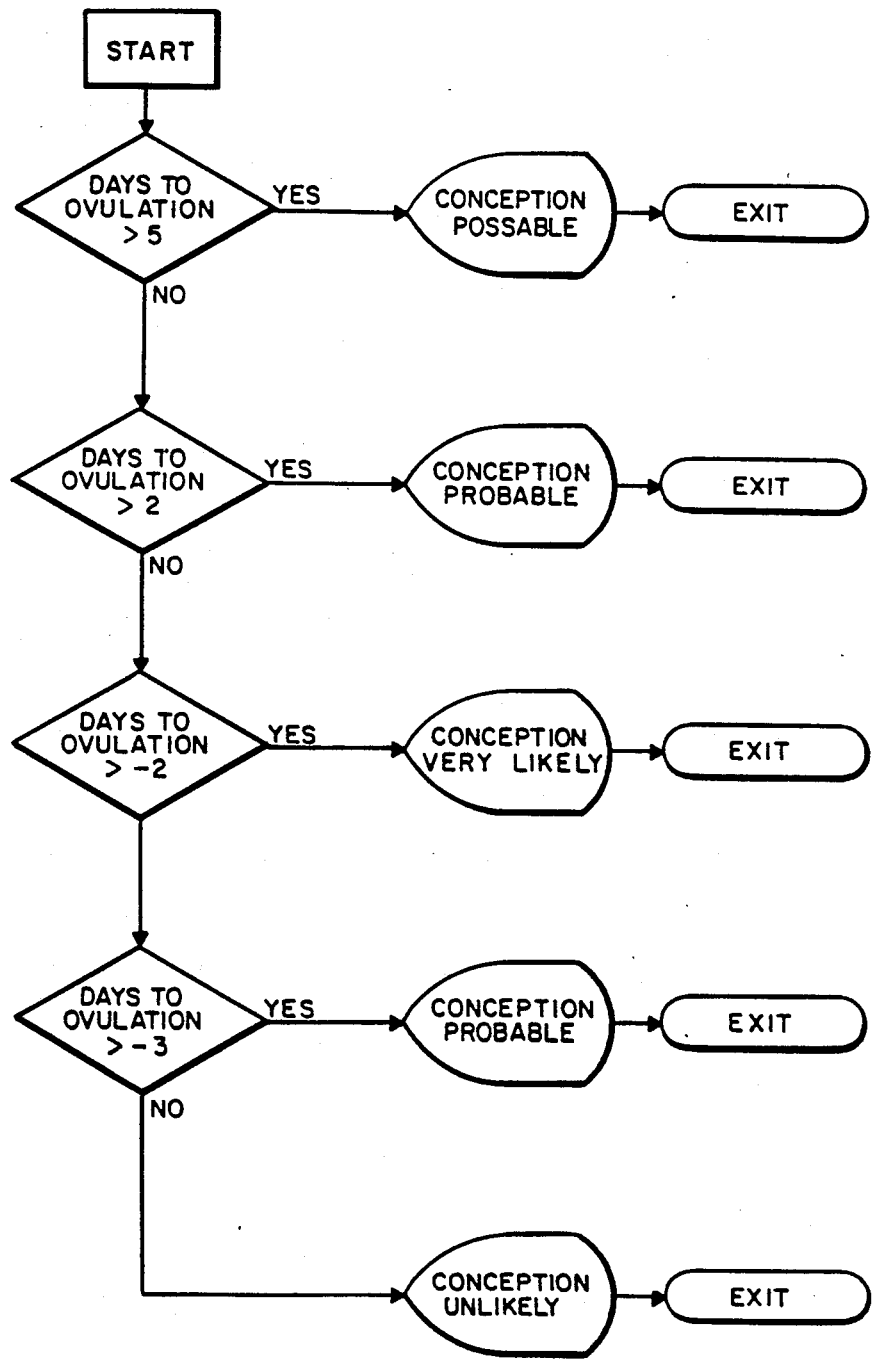
Fig_19

METHOD AND APPARATUS FOR PREDICTING AND DETECTING THE ONSET OF OVULATION

CROSS REFERENCE TO RELATED APPLICATION

This application is a continuation-in-part of earlier filed copending application Ser. No. 649,844, filed Sept. 11, 1984, abandoned.

BACKGROUND OF THE INVENTION

1. Field of the Invention

This invention relates to a method for the prediction and subsequent confirmation of ovulation during the menstrual cycle of the human female. More specifically, the invention relates to a method and apparatus for the accurate discrimination of the fertile phase from the non-fertile phase of the menstrual cycle of the human female.

2. Description of the Prior Art

The need for a simple but reliable method of predicting and confirming ovulation, which is conveniently carried out in the privacy of the home, has been a recognized need for many decades. Because of religious, philosophic, or health considerations, the preferred method of birth control for many is by periodic abstinence, also known as the "rhythm method." This method involves the identification of the fertile period using an available method, or more often simply by a guess based on the length of the menstrual cycle, and then avoiding coitus during this period. Ovulation is assumed to occur midcycle, and the period of abstinence is adjusted accordingly. This technique has proven highly unreliable at best. The unreliability of the rhythm method is largely due to the inability to accurately predict and confirm ovulation. Thus, a clear need exists for a natural family planning method with improved reliability.

A more reliable procedure, known as the symptothermal method, involves a subjective evaluation of basal body temperature and cervical mucus to determine the fertile period. This method requires intensive user training in the method and relatively high failure rates were and are still unavoidable.

In another procedure, changes in cervical mucus are combined with basal body temperature (BBT) to identify the onset and end of the fertile period. There are several disadvantages with this approach, some of them being the need for immobility before taking the temperature, daily monitoring of the cervix and vagina, and subjective interpretation of vaginal mucus quality and of the BBT trend. The technique is difficult to learn, with one to six months of careful training and supervision being required to acquire proficiency. Another relatively serious problem is the variation of the relation between the basal body temperature and the peak mucus symptom. In one study, in twenty-five of the cases, the temperature rise occurred more than 2 days before or 2 days after the peak symptom. Liskin, L.A., "Population Reports," Vol. 9, No. 4, pp. 33–65, Sept. 1981. Furthermore, basal body temperature reflects ovulation in only about 70 of the cycles, since monophasic (non-indicative) basal body temperature curves are frequently seen in ovulatory cycles. Bauman, J. E., "Fertility and Sterility," Vol. 36, pp. 729–733, Dec. 1981. When used for birth control, failure rates of up to 34% have been recorded with this method. Although computerized interpretation of data is now available for the sympto-thermal method as disclosed in U.S. Pat. No. 4,151,831, issued May 1, 1979, to R. W. Lester for "Fertility Indicator" and in published PCT Patent Application Pub. No. WO 83/01735, published May 29, 1983, on an application filed Sept. 30, 1982, by H. Schneider, for "Apparatus and Method for Determining Fertility Status", the disadvantages inherent in the physiological parameters used in the method are still limiting factors.

The identification of a preovulatory rise in estrogens followed by a peak in luteinizing hormone (LH) concentration as determined by radioimmunoassay is a good indication of imminent ovulation. Frequently, several samples of blood, drawn at mid-cycle, will be analyzed for luteinizing hormone concentration. These techniques are expensive and require several visits to a hospital or medical laboratory having the appropriate analytical facilities.

The process of ovulation can also be monitored and detected using ultrasonography. Daily visits to a center equipped with the sophisticated instrumentation used for the procedure are necessary. Several scans are required by mid-cycle to pinpoint ovulation by observing follicular development and subsequent ovum release. While accurate identification of ovulation is possible with this technique, it is of little value as a self-monitoring method for purposes of enhancing or reducing fertility.

Several methods of predicting ovulation based on biochemical changes in various body fluids such as vaginal secretions, saliva, or urine have been proposed. The major drawback of such methods is the significant variation in the component being measured between individuals. In one method, where the lactic acid concentration of vaginal secretions was proposed as an indicator of impending ovulation, the variability of its concentration between individuals was as great as one thousand percent. See U.S. Pat. No. 4,010,738, issued Mar. 8, 1977, to G. Preti, et al., for "Method of Predicting and Detecting Ovulation."

As a practical matter, it is generally believed at the present time to be impossible to design a chemical indicator system that is applicable to all women. One example of such a problem is related to the alkaline phosphatase levels of saliva which, although appearing to be predictive of ovulation, show such variations among individuals that any chemical means of monitoring for its changes requires that tests be individually calibrated to each user. See U.S. Pat. No. 3,406,005, issued Oct. 1968 to Foster. Methods based on analysis of urine for steroid hormones or their derivatives are subject to the same problem.

OBJECTS AND SUMMARY OF THE INVENTION

The principal object of the present invention is to provide a simple, inexpensive, and practically workable method for predicting and confirming ovulation.

A related object is to provide a method for identification of the fertile period, by means of a simple, reliable self-monitoring home test.

Another object is to provide a method of the foregoing character which uses a readily testable or measurable body element. More specifically, it is an object of the invention to use a measurable body fluid such as saliva.

A further object of the invention is to provide an improved apparatus for carrying out the method of the invention.

Still a further object of the invention is to provide easily used, simple apparatus such as probes, digital readouts, and indication lights or signals.

In accordance with the foregoing objects, the present invention is embodied in a method and apparatus for predicting the ovulation and fertile period of a human female. The method involves essentially measuring the electrical resistivity of the user's saliva, and by observing peaks and nadirs of changes in the saliva resistivity, predicting ovulation and fertility periods. The onset of ovulation can be further established by measuring the electrical resistivity of vaginal mucus, which, during the fertile period, shows a nadir on the day immediately preceding ovulation.

The apparatus utilized involves a probe for measuring resistivity together with an electronic circuit for indicating resistivity values. The values may be either plotted or fed to a microprocesser which, depending upon the previous history of the user, gives an appropriate signal indicating the onset of ovulation and fertility.

DESCRIPTION OF THE DRAWINGS

FIG. 3 is a block circuit flow diagram of apparatus for determining electrical resistance using a probe of the character shown in FIGS. 5–10.

FIG. 3A is a detailed circuit diagram showing the lockout circuitry for automatic recharging of a battery.

FIG. 5 is a plan view of the head portion of an oral probe used in the method of the present invention.

FIG. 6 is a sectional view taken substantially in the plane of line 6—6 of FIG. 5.

FIG. 7 is a plan view of the head portion of a modified form of oral probe.

FIG. 8 is a sectional view taken substantially in the plane of line 8—8 of FIG. 7.

FIG. 9 is a plan view of the head portion of a vaginal probe used in the method of the present invention.

FIG. 10 is a sectional view taken substantially in the plane of line 10—10 of FIG. 9.

FIG. 11 is a plan view of an apparatus embodying the present invention.

FIGS. 12–19 are logic flow charts showing the software algorithms for pattern recognition of resistivity values of the present invention.

DESCRIPTION OF THE PREFERRED EMBODIMENTS

The present invention involves a simple method that has been developed whereby ovulation and the fertile period can be predicted and accurately identified in the human female. This method results in a reliable self-monitored home-test. It can also be used by a physician in the treatment of female infertility since many diagnostic or therapeutic measures depend on the accurate prediction and detection of ovulation. The method further lends itself to this task due to the relative ease of measuring saliva electrolyte compositions through electrical characteristics. Saliva is a complex system containing several electrolytes including salts of sodium and potassium and non-electrolyte components including several proteins, enzyme systems, and immunoglobulins. The inherent limitations of chemical tests caused by inter-subject variability do not affect this system. Although variability in salivary electrical resistance (SER) between subjects does exist, the measurement of an electrical characteristic combined with the wide range afforded by a digital display provides precise measurement over varying SER baselines and amplitudes. Thus, the identical instrument can be used by all subjects without adjustment or individual calibration. This is specifically a result of the fact that the method of this invention refers to changes in trend and not to absolute resistance values.

Figure 1:
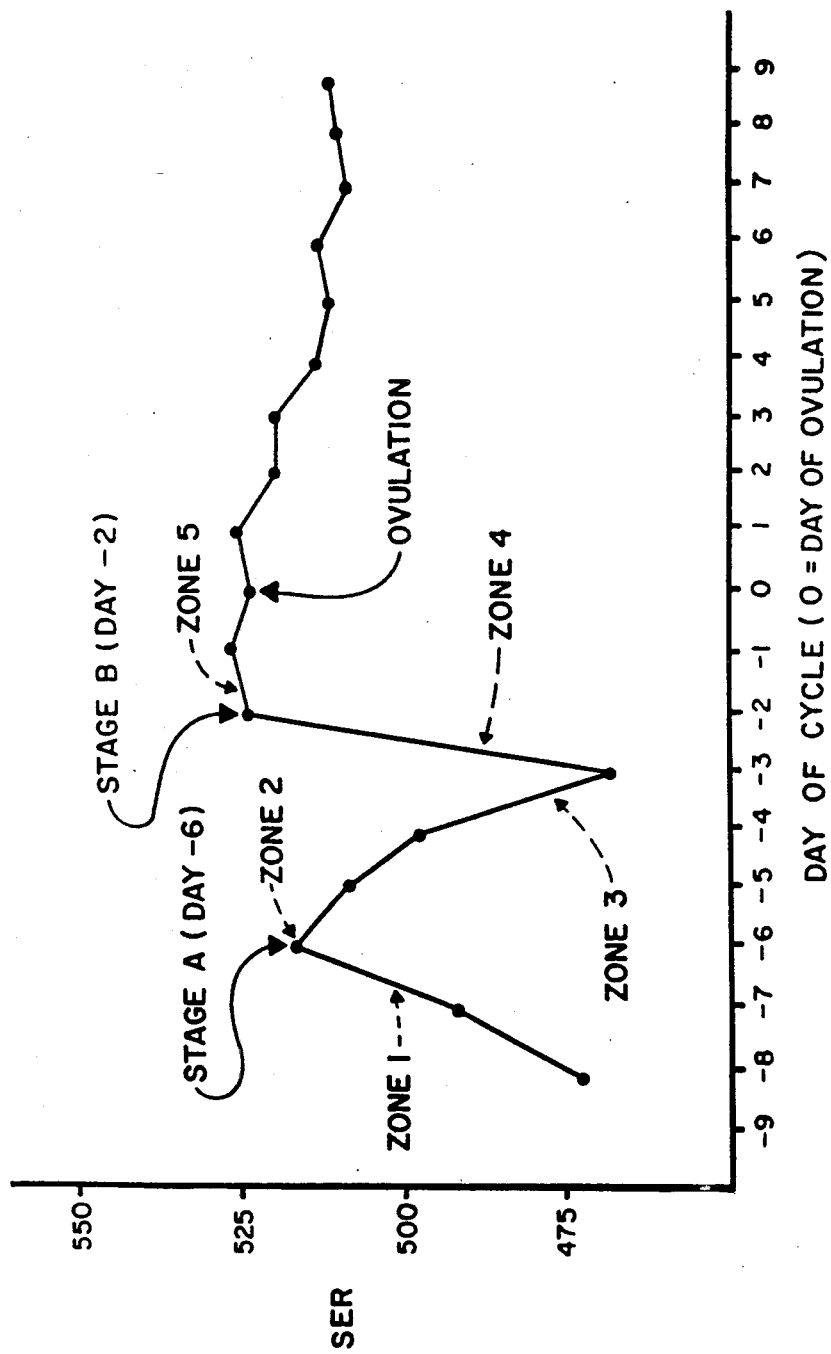
FIG. 1 is a diagram illustrating the pattern of salivary electrical resistance produced in accordance with the method of the present invention.

Using the present method, a user is able to predict the onset of her fertile period and the time of ovulation. To this end, the electrical resistance of the subject's saliva is monitored periodically, preferably daily, with an instrument designed for that purpose. Basically, one illustrative instrument, which is shown in the drawings and described in more detail below, consists of a housing containing a control circuit, with a digital display, a probe or sensor adapted to be placed on the user's tongue, and a vaginal probe. Measurements are begun on the fifth day of the menstrual cycle, where the first day of the menstruation is day one. Readings are taken at approximately the same time each day, preferably immediately after awakening and prior to toothbrushing, breakfast, and other morning activities. To take a reading, excess saliva is swallowed, but with the tongue in moist condition, the sensor is placed on the tongue about 2 cm from its tip and held with very light pressure. The salivary electrical resistance (SER) reading or value is observed on the digital display and is recorded. The readings are plotted, with day-of-cycle on one axis and the SER values, which values are dimensionless numbers proportional to resistance, on the other axis, as shown in FIG. 1. When the first peak in SER values is reached, i.e. when a decline in SER occurs after an initial rise, the first predictive stage has been reached, a first recognition signal is generated by the instrument based on reaching State A, shown as Stage A in FIG. 1. Regardless of variations in menstrual cycle length, Stage A occurs approximately six days prior to ovulation (on day 6, where day 0 is the day of ovulation). The occurrence of Stage A may vary by plus or minus one day. Even after accounting for this variation, Stage A occurs prior to the onset of the fertile period, which is assumed to be 72 hours prior to ovulation, and is therefore a good indicator of the imminent fertile phase of the cycle. Thus, if the user wishes to prevent conception, she is made aware of the onset of the fertile period sufficiently in advance so that she may abstain from coitus during this period The next predictive stage, Stage B in the SER values, can be recognized when a sharp increase in readings occurs following a nadir or sharp dip, as shown on FIG. 1. This SER value graphical pattern is recognized and causes generation of a second recognition signal. A distinct V-shaped pattern should appear in the graphed readings at this stage. Stage B occurs usually a day after the nadir and approximately two days before ovulation, but may vary by plus or minus one day. Stage B is a sign of imminent ovulation, and is useful for identifying the peak of the fertile phase and establishing the best time for coitus or insemination when the user desires to conceive Patients under the care of a physician may also be scheduled for other evaluations such as post-coital tests, hormone assays, or ultrasonography at this stage. Though ovulation will usually occur within two days after Stage B those wishing to avoid conception should abstain from coitus for about four days after Stage B.

Figure 2:
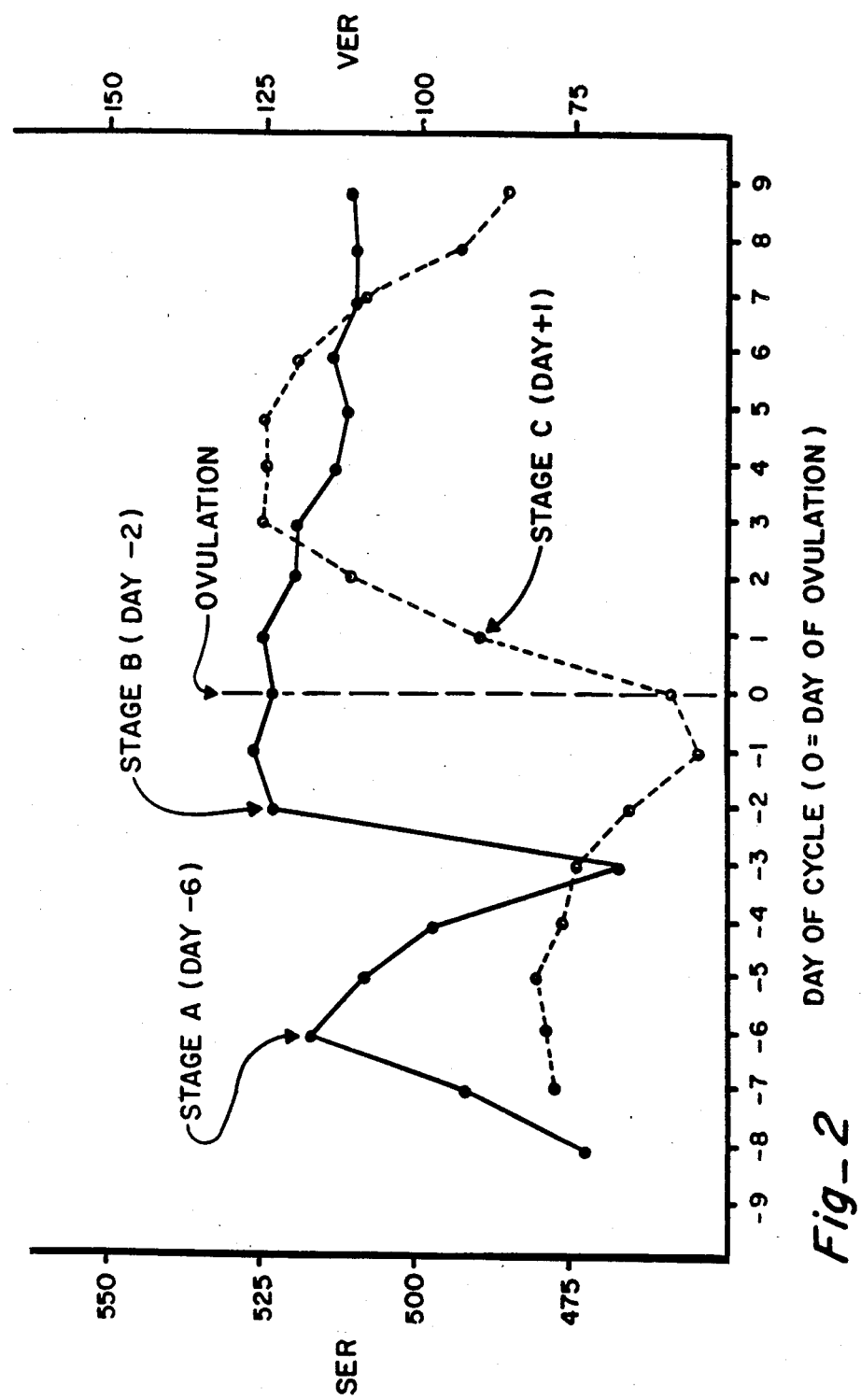
FIG. 2 is a diagram illustrating the pattern of salivary electrical resistance and vaginal electrical resistance produced in accordance with the method of the present invention.

While the changes in SER value during the menstrual cycle indicate the onset of the fertile period and ovulation, they do not confirm that ovulation has occurred. The present invention comprises a method of monitoring the concentration of and interaction between estrogen and progesterone through their effect both on the ionic concentration and the volume of cervical mucus. The abrupt decline in estrogen and the subsequent increase in progesterone at the time of ovulation cause marked changes in both ionic concentration and the volume of cervical mucus. These changes are monitored using an intravaginal probe that measures the electrical resistance (VER) or conductance of the vaginal mucus, and is sensitive not only to changes in the ionic composition of the mucus but also is sensitive to its volume. FIG. 2 illustrates diagrammatically the changes in both SER and VER as related to the menstrual cycle and ovulation. A marked increase in VER, after Stage B in SER, is an indication that ovulation has occurred (Stage C). This third pattern, in VER values rather than SER values, is recognized by the instrument and a third recognition signal generated. Thus, a reliable indication confirming ovulation is given in a rapid and simple to use home-test method. By combining the SER and VER readings, the test becomes even more accurate and reliable than when one reading alone is used.

The user is able to predict the onset of the fertile period and the time of ovulation by monitoring changes in both salivary electrical resistance (SER) and vaginal electrical resistance (VER) at mid-cycle to confirm the occurrence of ovulation. Determination of SER is carried out as described above; however, when Stage A in the SER is observed, the VER readings are obtained in addition to the SER. The VER readings are taken at approximately the same time each day. To obtain a VER reading, a special vaginal probe is connected to the control box used for the electrical resistance measurement and inserted into the vagina until it rests at the base of the cervix. The VER reading is simply observed on the digital display and recorded. The VER readings are graphed along with the SER values.

The interpretation of the SER values relative to Stages A and B is as described above. Because of the availability of midcycle VER measurements, a more precise confirmation of the occurrence of ovulation can be made During Stage B, the VER reading will be relatively low, reaching a nadir corresponding with the estrogen peak (FIG. 2). After ovulation has occurred, the sharp rise in progesterone together with the low estrogen levels result in a marked elevation in the VER readings. Thus, after taking the VER readings if the user observes a marked increase in VER, that is coincident with the stage of the cycle that follows Stage B, and may be taken as a reliable confirmatory indication of ovulation, as shown in FIG. 2. The fertile period begins about 72 hours before ovulation. The end of the fertile period is assumed to occur 48 hours after the VER increase. The period where probability of conception is high begins about four days after the VER increase and ends about four days after ovulation. In FIG. 2, the predictive indications of SER are combined with the confirmatory value of VER measurements, thus defining the fertile phase of the menstrual cycle. The use of the VER probe may be discontinued at the end of the fertile phase.

The task of recording and interpreting the SER and VER readings may be accomplished automatically. The instrument is compact, with a display screen and provision for accepting only either one of the SER and VER measuring sensors. The instrument automatically recognizes which sensor is being used. The instrument has separate calibrations for vaginal and salivary readings. Voltage from either probe is routed from the probe jack to the appropriately calibrated measuring circuit by means of matched portions of multi-input jack and multi-output plug sets. To obtain consistent data, the instrument obtains an integrated reading over a 5 second period, after an initial delay period of 3–5 seconds. The user manually enters the first day of her cycle so that the built-in microprocessor integrates the stage of the cycle, with the appropriate SER and VER data. Daily measurements are taken as described above, but with the readings being recorded in the instrument's memory. At the beginning of the cycle only the SER sensor is used.

By using a first algorithm for pattern recognition which is programmed into the instrument's microprocessor, the occurrence of Stage A is detected. Until Stage A is detected, the instrument's display shows that the probability of conception is low. When Stage A is reached, the display reads "Conception Possible". At this time, the instrument also alerts the user to begin VER measurements. When Stage B is detected by a second algorithm for pattern recognition, the display indicates that "Conception Very Likely". It monitors the VER readings until their abrupt increase indicates ovulation. From the beginning of Stage A until the occurrence of ovulation, the number of days to ovulation are displayed. After 72 hours has elapsed from the time of ovulation, the display shows that the probability of conception is low and reads "Conception Unlikely", since the end of the fertile phase has been detected. At this time, the instrument indicates to the user that VER readings may be discontinued for that cycle.

When a user first begins to use the instrument, the time of ovulation is predicted, first using the number of days to Stage A from the beginning of the cycle. The actual prediction of the time of ovulation, once Stage A is detected, is based on a regression equation which correlates statistical information gained from initial experiments. The SER and VER data, together with the length of each cycle, is permanently stored in the instrument's memory for up to two years, with provision for transfer onto a hard copy when required.

The method embodying the present invention is the basis of an accurate but simple home-test for determination of the fertile phase and ovulation during the menstrual cycle in women. It is clear that although the method may vary in degree of complexity and in the sophistication of instrumentation used, the process involved remains basically unchanged. It should also be clear that while the type of measurement used has been limited to electrical resistance, the basic principle involved in the method is the change in total electrolyte concentration of saliva and cervical/vaginal mucus. An equally viable method may be obtained using electrical conductance or impedance For determining and indicating salivary electrical resistance or vaginal electrical resistance, there are provided appropriate probes and electronic apparatus as shown in FIGS. 3 through 10. Referring to FIG. 3, the salivary electrical resistance measuring and indicating apparatus is embodied in a circuit 10 which includes an alternating voltage square wave generator 20 powered by a battery or power supply 21 connected through a combined on-off and battery test switch 22. The generator 20 is a "run-up run-down" RC oscillator using an operational amplifier integrated circuit. The two halves of the cycle are matched by trimming the timing components. The output of this oscillator is a symmetrical square wave with a swing of an essentially fixed amount less than the supply voltage. This square wave is applied, through a capacitor and a series resistor, to the probe 24. The voltage across the probe is thus a symmetrical square wave equal to the oscillator output divided by a voltage divider consisting of the series resistor and the probe/medium resistance.

An excessive voltage protection switch 25, which consists of two diodes, is connected across the probe jack These diodes limit the voltage to the probe to a predetermined maximum level to protect against any possibility of trauma or discomfort to the user.

The probe output signal is fed to an amplifier 26. The amplifier is an operational amplifier system utilizing the same integrated circuit package as the oscillator. Substantial negative feedback is used so that its gain is constant. The gain is adjustable for calibration purposes by use of a variable resistor or of a selected fixed resistor. The signal from the probe is capacitively coupled to its input, and the reference voltage of the amplifier system is half the supply voltage.

The output of the amplifier is essentially a square wave averaged by a long-time-constant resistance/capacitance circuit or commutator 28. The voltage between the amplifier output and this average is connected, through two field-effect transistor (FET) bilateral switches, to the measuring circuit during one half of the cycle and in the opposite polarity during the other half of the cycle. Thus, the output is rectified, and a dc voltage proportional to the resistivity of the biological fluid is applied to the measuring circuit. The oscillator square wave is used to control the switches through an inverter 29.

The measuring circuit 30 is connected to a liquid crystal display 31. The output of the commutator 28, now dc, is applied to this measuring circuit after smoothing by a resistance-capacitance filter circuit 32. This voltage is proportional to the probe/medium resistance, to the oscillator voltage swing, and to the amplifier gain. A run/hold switch 34 is provided external to the integrated circuit to hold and/or store a desired reading on the display.

The specific digital reading of the measuring circuit is selected to provide for the best possible resolution of the time-measurement curve for the particular fluid being measured. The signal voltage, adjustable by gain for calibration as mentioned above, varies as the supply voltage changes. A suitable voltage is derived from the battery voltage for the reference voltage to compensate for changes in battery voltage. Since the oscillator output is approximately the battery voltage less a fixed amount, a similar part of the battery voltage, a fraction of the battery voltage less a suitable fixed amount, is used as the reference voltage. This renders the reading essentially independent of the battery voltage, eliminating the need for a regulated voltage, and reducing the supply voltage required.

Power is supplied by a pack of nickel cadmium rechargeable battery cells, by disposable batteries or by any suitable battery or other power source. A low battery voltage detector 35 compares a fraction of the battery voltage to a different fraction of the voltage across a Zener diode. This diode is also used to obtain the compensating voltage for the reference, as described above.

The low battery voltage recognition circuit (see FIG. 3A) is set to a selected voltage appropriate to the power supply. For instance, for a 9-volt battery it is set at 7 volts. When the battery voltage drops to that level, the low battery voltage recognition circuit activates one or more elements on the liquid crystal display, thus informing the user that the battery needs replacement or recharging.

The microprocessor-driven instrument is powered by nickel cadmium batteries. It is contemplated that, once placed in service, the instrument will normally be connected to the charger except during the process of taking readings To prevent the taking of readings with the charger connected, the program checks for voltage at pin 1 of IC22. If the charger is connected, the instrument cannot be turned on.

The battery voltage is checked by comparison circuits at IC23 and if the voltage is less than 6.2 V and the charger is connected, a charge cycle is initiated by IC23 through IC20, a flip-flop.

A modification of the above circuit involves adding an accurate inverter after the amplifier so that both polarities of the signal may be connected alternately to the "high" terminal of the measuring circuit by two bilateral switches. The "low" terminal of the measuring circuit is then directly connected to the average of the amplifier output and the inverter output, thus requiring much less filtering of the signal average Since only a single operational amplifier is sufficient for the main amplifier, and the other operational amplifier can be used as the inverter, without increasing the complexity of the circuit.

The analog to digital (A/D) converter includes a terminal which is maintained internally at a voltage that is a fixed amount (x) less than its supply voltage (y). Amount x is approximately equal to the amount that the square wave output differs from the supply voltage. Thus a fraction of this voltage (y-x) can be used as reference for the A-D (analog to digital) conversion and x can be used as the reference for the low battery voltage indicator.

Figure 4:
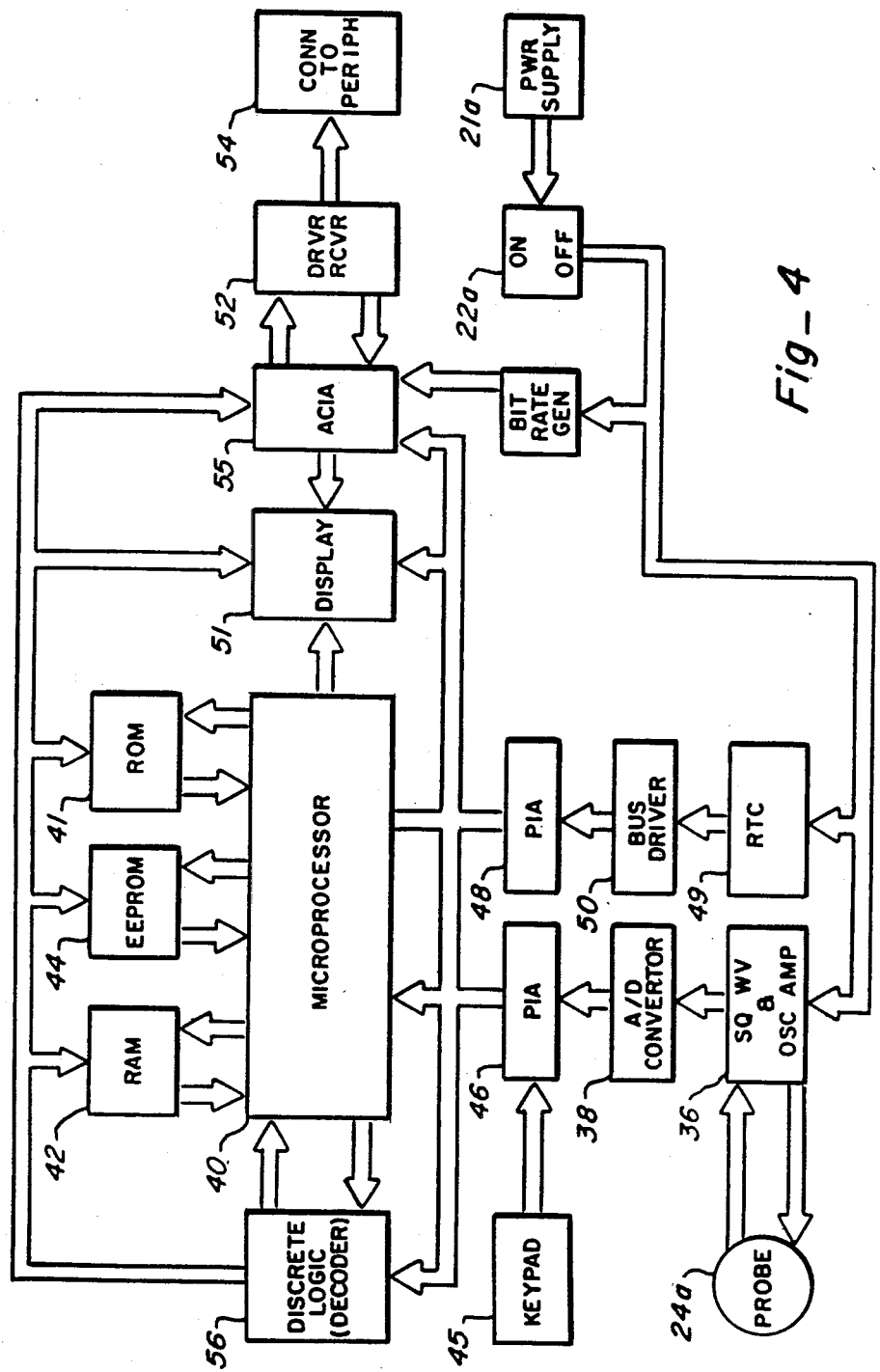
FIG. 4 is a block flow diagram of apparatus using a microprocessor for indicating fertility status in accordance with the present invention.

Another embodiment of instrumentation for applying the method of the present invention includes a microprocessor for data processing and for storing the pattern recognition algorithms, is shown in FIG. 4. This embodiment of the method utilizes several elements to process the measurements obtained by a circuit like that shown in FIG. 3 described above. These elements include a power supply 21a, an on-off switch 22a, and a square wave generator and amplifier measuring circuit 36 receiving signals from a probe 24a. The voltage derived from the measuring circuit 36 is fed to an A/D (analog to digital) converter 38, which is used to convert the analog probe signals to digital values for processor input to a microprocessor 40 utilizing a monitor program.

The monitor program is the system software. It defines the order of events, the interpretation of data, and the resulting conclusions. The microprocessor 40 is the controller of the system. It executes the monitor program, which is stored in the read only memory (ROM) 41. A programmable clock is used to supply the current time and date. Random access memory (RAM) 42 is a read/write static memory element. It is used to store temporary data values and the microprocessor stack. Data values including in part SER and VER daily values are retained in the electrically erasable programmable read only memory (EEPROM) 44, which is a non-volatile read/write memory element.

A telephone-type 12-key pad 45 or a similar membrane switch is provided for user input, such as time and date, set or reset routines. Two peripheral interface adapters (PIA), in the form of integrated circuits 46, 48, are used to interface between the microprocessor bus and peripheral devices. Both are used for input to the processor. One handles the keypad and the A/D converter; the other handles the real-time clock 49 through the bus driver 50.

Processor output is displayed by a two-line, 32-character liquid crystal display (LCD) 51. A buffer circuit is included in the integrated circuit of the display. In order to change parallel data from the processor to serial, properly synchronized data for a communications link, such as to another computer 52 or a peripheral device 54 and vice versa, there is provided an asynchronous communications interface adapter (ACIA) 55. Discrete logic digital gate decoders 56 are provided to decode the microprocessor control and address signals for addressing other system elements.

The microprocessor system requires a 5-volt dc voltage supply. In one embodiment, the power supply circuit converts line voltage into the required voltage. The power supply 21a also includes five nickel cadmium batteries so that measurements can be taken with the device disconnected from the line voltage. This also allows for portable operation and standby protection against temporary interruptions of the main current.

The software for the device consists primarily of a continuous loop that looks for any input from the keyboard and goes to the appropriate routines; second, the real-time clockcalendar is read to see if the day has changed. The MAIN routine shows a test for RESET. This will be handled by the microprocessor with an appropriate jump to the RESET routine or by a keyboard RESET. RESET will return to the main loop with the microprocessor in a known state. Data will not be destroyed or lost if the device is reset.

In the initial logic step in the software, an SER reading is always taken and a delta value for the difference between the present day SER reading and the SER reading of the prior day is obtained, the absolute value of delta (SER) being stored in the EEPROM 44 (FIG. 4), an internal, non-volatile memory means of the instrument. As seen in FIG. 1, the days of the menstrual cycle prior to ovulation are broken down into 5 distinct zones. Zone 1 is separated from Zone 2 by Stage A. A significant drop in delta (SER), for example ten or more, signals a change from Zone 2 to Zone 3. Zone 3 changes to Zone 4 after the nadir of the SER curve occurring approximately 3 days prior to ovulation. Stage B separates Zone 4 from Zone 5, during Zone 5 ovulation occurs. The software logic of the instrument always initially assumes the instrument is used within five days of the start of menstruation.

As described above, the stages A and B of the SER data, and the post ovulation rise in VER, stage C (FIG. 2), are determined by three algorithms for "pattern recognition" incorporated into the electronic circuitry of the instrument. The cycle day prior to the first negative slope in the SER graph of FIG. 1, detected after cycle day 5, is found by a first algorithm shown in FIG. 12 for pattern recognition, which generates a first recognition signal indicating the day of the cycle of Stage A to the memory. In determining a positive or negative slope, allowance is made for non-significant variations of noise. Once a negative slope is measured between sequential SER readings, an absolute difference or delta (SER) in sequential SER readings of a predetermined amount greater than any noise value that might be encountered is detected by the electronic measuring circuitry embodying the first algorithm. The predetermined amount used in the present invention is 7. The threshold between non-significant and significant variation is greatly affected by the sensitivity of the measuring circuit, and must therefore be defined accordingly. Since the basic method of this invention is based on changes in trend rather than on absolute values, the sensitivity of the measuring circuit or the threshold for "noise" need not be defined.

In the algorithm of FIG. 12, no VER measurement is needed, as the user is still in Zone 1 and Stage A has not been reached. A VER measurement is needed to correlate the day of ovulation, as has been previously discussed, and is pictorially seen in FIG. 2. Delta (SER) measurements on sequential days are determined by simply subtracting the immediately previous day's SER reading from the present day's SER reading. Depending upon whether the delta (SER) value is positive or negative, the user will be on one side or the other of Stage A of the SER curve. If Stage A has not been reached, delta (SER) will be positive, as is the slope of the SER graph while the user is in Zone 1. The slope of the graph and the delta (SER) values are negative for Zone 2, after Stage A has been reached. The microprocessor stores this first algorithm for pattern recognition as well as the day of the cycle upon which Stage A is reached for use in determining ovulation in the present menstrual cycle and for later use in a regression equation used to calculate the day of ovulation.

As seen in FIG. 12, if the magnitude of delta (SER) is negative and its magnitude is greater than 7, to account for non-significant variations or noise, then Stage A has been determined to be the previous day of the cycle and the loop continues to the algorithm for recognition of Zone 2 found in FIG. 13.

With respect to FIG. 12, should the difference or delta (SER) be greater than zero, the software either implements the days to ovulation sub-routine of FIG. 18 or, if the delta is approximately zero, the present SER value is compared to two consecutive previous readings to find out if a total delta (SER) between the present values and the first of the two previous values greater than 7 has occurred. If a delta greater than 7 in magnitude between the present and first of the three consecutive SER values has occurred, then Stage A is assumed to have occurred 2 days prior to the present measurement and the logic of FIG. 13 relative to Zone 2 is implemented.

It should be noted that all of the logic flow charts ultimately lead to the flow chart seen in FIG. 18. If no VER is needed, the SER reading is displayed for recording and the intelligence and the display are then disabled. If a VER reading is needed and point A has been reached, then a regression equation seen FIG. 18 is utilized to calculate the day of the cycle during which ovulation will occur. Depending on whether ovulation has passed, a message will indicate days to ovulation. Whether or not ovulation has passed, a message will be displayed to the user based upon the logic of FIG. 19 indicating the probability of conception.

In FIG. 13 Stage A has passed and the user of the instrument is taking measurements at a day of the cycle within Zone 2. From this point on through ovulation, an indication will be given to the user that a VER measurement is needed. A second algorithm for pattern recognition is embodied in the logic of FIGS. 13, 14 and 15 to recognize the nadir in the SER values of FIG. 1. Once the nadir is detected by the second algorithm, a second recognition signal corresponding to the day of the cycle at which State B occurs is generated and stored to memory. FIG. 13 finds a difference between the present SER reading and the SER reading at Stage A that is of a magnitude greater than 10. The magnitude is selected so as to be large enough to indicate that Zone 3 has been reached. Once Zone 3 has been reached, then the logic flow chart of FIG. 14 is controlling. Again, in Zone 3 a VER reading is needed and so indicated. The difference in sequential readings of SER, again referenced to as delta (SER) in FIG. 14, needs to be greater than zero, indicating a positive slope in the SER measurement graph of FIG. 1, and that Zone 4 has been entered after the drop in SER values from Stage A to the nadir. The logic associated with Zone 4 is shown in FIG. 15 again displays to the user the need for a VER measurement to correlate with the SER measurement being taken. The logic of FIG. 15 is searching for Stage B through use of the second algorithm for SER pattern recognition incorporated within the microprocessor of the electronic circuitry shown in block form in FIG. 4. Three consecutive daily values of SER will establish the nadir for which the second algorithm for pattern recognition is searching. Again a change in slope to negative or zero slope is the pattern which is recognized by the algorithm of FIG. 15 to establish the day of Stage B. The second algorithm searches for a significant drop in SER from Stage A, a change in slope, i.e., an increase in SER values after a decrease.

From Zone 4 the Zone 5 software subroutine is seen in FIG. 16. The day of the cycle corresponding to Stage B has been found through the logic shown in FIG. 15. The logic shown in FIG. 16 simply determines how many days since Stage B has been reached, and if greater than 1, indicates that day of ovulation has been reached. Such a calculation follows the experimentally found result that Stage B is usually followed in 2 days by ovulation as indicated in FIG. 1. This logic will however, be overriden when VER measurements are available.

In any of the previous software sub-routines relating to Zones 2 through 5, where a VER measurement is indicated, the respective logic flow paths are followed and then a VER measurement is taken and the logic flow path shown in FIG. 17 is operative. As seen in FIG. 17, a third algorithm for pattern recognition of Stage C of the VER measurement graph of FIG. 2 first compares sequential VER measurements until the VER measurement is greater than the minimum VER which would occur prior to the day of ovulation. After minimum VER is determined and stored, the algorithm associated with VER pattern recognition then determines Stage C by searching for an increase in consecutive VER values or delta (VER) of greater than 25.

When Stage C has been recognized by the third algorithm shown in the flow chart of FIG. 17, then the minimum VER measurement seen at day minus 1 in FIG. 1 and FIG. 2 and the day of ovulation are both stored to memory by a third recognition signal generated by the third algorithm for later print-out in graphical or tabular form as desired. The determination of the day of ovulation by the third algorithm supersedes any finding based on SER values and the days to ovulation flow chart shown in FIG. 18 and causes the instrument memory of the microprocessor to store the day of ovulation found by the third algorithm.

The day of ovulation is normally predicted using the regression equation of FIG. 18 once Stage A is detected. The independent and dependent variables used for the equation are days to Stage A and days to ovulation respectively, from the beginning of the cycle. The first equation is initially derived from statistical information gained from prior experiments ments and users. As data accumulates for a given individual user, these equations are weighted to reflect the cycle characteristics of the user. Data used for this purpose will include days to Stage A, days to Stage B, days to ovulation, and the length of the user's menstrual cycle, all of which will be stored in the memory of the microprocessor.

Several suitable designs have been developed for transducers to measure the SER and VER, as shown in FIGS. 5 through 10. Each probe consists of one or more active electrodes and one or more ground electrodes. The electrodes are mounted in a non-conductive, biologically inert material such as epoxy or acrylic plastic. They are connected to the measuring circuit by two or more shielded conductors, which may be connected to the instrument with a plug and jack or by hard wiring to the circuit board of the measuring instrument.

The geometry of the probe is determined by the configuration of the site of its intended use. A shaft and handle facilitate vaginal use, while the oral probe is a small disk, a modified disk with a handle molded onto it, or a cylinder with rounded ends with or without a shaft or handle.

The electrodes, of any appropriate conductive material such as gold, silver, sometimes with an admixture of silver chloride, copper, aluminum, or stainless steel, may be embedded in or applied to the surface of the non-conductor. Sets of two or more stainlesss steel rings are wired alternately to form a series of active and a series of ground electrodes. Two or more silver/silver chloride, gold, or stainless steel disks are connected in two series. Interlocked patterns of conductive material are etched from a metal coating on a non-conductive surface using printed circuit board technology, or they may be applied to a ceramic substrate. A combination of rings and disks may also be used, as well as a combination of electrodes with two pairs of connectors to the measuring circuit, which would serve to localize the readings within the site.

Illustrative oral probes are shown in FIGS. 5-8. The preferred oral probe comprises a generally lollipop-shaped probe having a round head 60 integral with a handle 61. The head 60 and handle 61 are formed with a flattened surface 62 in which a plurality of electrodes or contacts 64, 65, 66 are embedded. Appropriate wires or conductors 68 are molded into the probe and connect the respective electrodes to a wire leading to appropriate terminals or jacks adapted to be secured to the processing unit amplifier 26 and voltage limiter 25. The electrodes are molded to be flush with the flattened surface so as to provide a smooth continuous surface in order to prevent injury to the user's tongue or mouth. The probe contacts may comprise gold-plated button electrodes. Any two buttons can be electrically connected to form a common electrode.

A modified form of probe head is shown in FIG. 7. In this modification the head is a generally elongated oval or elliptical member connected to a handle (not shown). A plurality of chevron-shaped electrodes 71, 72 are mounted in a flattened surface 74 of the head 70. The respective electrodes 71, 72 are connected by appropriate wires 75, 76 extending to the processing unit. The electrode assembly of the modification shown in FIG. 7 is conveniently formed as a double-sided printed circuit board 80 with the electrodes 71, 72 plated on one side and connecting strips plated on the opposite side and connected to the conductors 75, 76, which exit the probe and are connected to the processing unit by an appropriate plug or jack.

An illustrative vaginal probe is shown in FIGS. 9 and 10. This probe comprises a rounded cylindrical probe element 90 with alternating pairs of ring electrodes 91, 92 embedded in the surface and an electrode cap 93 defining the tip end of the probe 90. The rings and cap are embedded so as to provide a smooth exterior surface. The rings and cap may be formed of stainless steel or like material. Each set of rings and cap is connected to a wire 94, 95, respectively, also embedded in the probe and extending through the probe handle 96 for connection to the processer.

The various ring electrodes may be connected so as to not only give a measure of the electrical resistivity of vaginal mucus, but also to give a quantitative indication of the volume of mucus.

The processing unit itself may be of any appropriate design configuration and will generally include, as shown in FIG. 11, a housing 100 suitable for hand use, with a digital readout display 101 and a keyboard 102. Additional control buttons, on-off switches, etc. may be utilized.

While a certain illustrative method and apparatus embodying the present invention has been shown in the drawings and described above in considerable detail, it should be understood that there is no intention to limit the invention to the specific forms and embodiments disclosed. On the contrary, the intention is to cover all modifications, alternative constructions, equivalents, methods and uses falling within the spirit and scope of the invention as expressed in the appended claims.

We claim:

1. A method for predicting ovulation in a human female subject, comprising the steps of noting the onset of menstruation of the subject, making daily determinations of the electrical resistivity of the subject's saliva beginning not more than five days following beginning of menstruation, and indicating the onset of ovulation as a function of a peak resistivity measurement following onset of menstruation, which peak is followed by a nadir and subsequent sharp increase in said electrical resistivity measurement.

2. A method for predicting ovulation in a human female subject, comprising the steps of noting the onset of menstruation of the subject, making daily determinations of the electrical resistivity of the subject's saliva beginning not more than five days following beginning of menstruation, and indicating the onset of ovulation as a function of a peak resistivity measurement following onset of menstruation, which peak is followed by a nadir and subsequent sharp increase in electrical resistivity measurement, said peak occurring about six days prior to day of ovulation and said sharp increase occurring about two days prior to onset of ovulation.

3. A method for predicting ovulation in a human female subject comprising the steps of obtaining and storing information with respect to the subject's menstrual cycle and the resistivity of the subject's saliva, and processing such stored information to statistically predict the fertility status of said subject in response to peaks and nadirs of resistivity following onset of menstruation.

4. A method for predicting ovulation in a human female subject comprising the steps of obtaining and storing information with respect to the subject's menstrual cycle and the resistivity of the subject's saliva, and processing such stored information to statistically predict the fertility status of said subject in response to peaks and nadirs of resistivity following onset of menstruation, the peak resistivity following the beginning of the menstrual cycle indicating onset of ovulation within about six days, and a nadir following said peak and in turn followed by a sharp increase in resistivity indicating onset of ovulation in about two days.

5. A method of indicating the onset of ovulation in a human female subject comprising the steps of determining the resistivity of the subject's saliva at daily intervals, observing increases and decreases in said resistiivity, and giving a signal upon a predetermined sequence of an increase and a decrease in said resistivity to indicate the onset of ovulation in the subject.

6. A method as defined in claim 5 wherein said decrease in resistivity is followed by a sharp increase in resistivity, indicating the occurrence of ovulation within the following two days.

7. A method of predicting ovulation and the fertile period in a human female subject having a menstrual cycle, comprising the steps of determining the electrical resistivity of the subject's saliva on the day of the menstrual cycle beginning not more than five days after onset of menstruation, making a daily measurement of the saliva resistivity, determining a first peak of electrical resistivity value following the onset of menstruation, which peak indicates that ovulation will occur in about six days, and determining a sharp rise in resistivity following an observable nadir, said sharp rise in resistivity indicating that ovulation will occur in about two days, thereby accurately indicating the onset of ovulation and the fertile period in a subject.

8. A method of diagnosing the onset of the fertile period or ovulation in a female subject, comprising the steps of monitoring the variation in resistivity of the saliva of the subject and providing an indicator means for qualitatively and quantitatively responding to the resistivity of the saliva of said subject whereby the response of said means is diagnostic of the onset of the fertile period or ovulation in said subject.

9. A method for predicting ovulation and the fertile period in a human female user having a menstrual cycle, comprising the steps of determining the electrical resistance of the user's saliva on the day of the menstrual cycle beginning not more than five days after onset of menstruation, making a daily measurement of the salivary electrical resistance, plotting the electrical resistance measurement value on a daily basis, determining the first peak of the plot of electrical resistance values, which peak indicates that ovulation will occur in about six days, and determining the next peak of the plot following an observable nadir, said next peak indicating that ovulation will occur in about two days, thereby accurately indicating the onset of ovulation in the user.

10. A method as defined in claim 9 wherein said first peak of the plot of electrical resistance values represents an increase of at least about 10 percent.

11. A method of predicting ovulation and the fertile period in a human female user as defined in claim 9, further including the steps of determining the electrical resistivity of the user's vaginal mucus beginning at the time of detection of the first peak of the plot of salivary electrical resistance values, plotting the vaginal electrical resistance measurement value on a daily basis, and determining a nadir followed by a rise in vaginal electrical resistivity indicating ovulation in the user.

12. An instrument for use in predicting ovulation in a human female subject comprising means for making daily measurements of the electrical resistivity of the subject's saliva, and means for indicating the onset of ovulation in response to a peak resistivity measurement following onset of menstruation followed by a nadir resistivity measurement and a subsequent sharp increase in electrical resistivity measurement 13. An instrument for use in predicting ovulation in a human female subject comprising means for determining the resistivity of the subject's saliva, means for obtaining and storing information with respect to the subject's menstrual cycle and the resistivity of the subject's saliva, and means for processing such stored information to statistically predict the fertility status of said subject in response to peaks and nadirs of resistivity following onset of menstruation.

14. An instrument for indicating the onset of ovulation in a human female subject comprising means for determining the resistivity of the subject's saliva at daily intervals, means for observing increases and decreases in said resistivity, and means for giving a signal upon a predetermined sequence of an increase and a decrease in said resistivity to indicate the onset of ovulation in the subject.

15. An instrument for diagnosing the onset of the fertile period or ovulation in a female subject comprising means for monitoring the variation in resistivity of the saliva of the subject, and means for qualitatively and quantitatively responding to the change in resistivity of the saliva of said subject and producing a signal diagnostic of the onset of the fertile period or ovulation in said subject.

16. A method of predicting ovulation in a human female subject, comprising the steps of making daily determinations of the electrical resistivity of the subjects saliva beginning not more than five days following the onset of menstruation by applying a first sensor for forming analog data signals representing salivary electrical resistivity, converting said alalog data signals to digital data signals, processing said digital data signals over a predetermined time to obtain a digital data signal representing the current daily value of the salivary electrical resistivity, storing said daily salivary electrical resistivity values in memory, applying a first algorithm for pattern recognition to the stored values, and generating a first recognition signal in response to the first occurrence of the current daily value being less than the previous daily value by more than a predetermined significant amount.

17. The method of predicting ovulation as defined in claim 16, further comprising the step of displaying a signal indicating a high probability of conception in response to generation of said first recognition signal.

18. The method of predicting ovulation as defined in claim 16, wherein said step of processing said digital data signals over a predetermined time comprises integration.

19. The method of predicting ovulation as defined in claim 16, further comprising the step of digitally displaying said current value resulting from said processing step.

20. The method of predicting ovulation as defined in claim 17, further comprising the steps of applying a second algorithm for pattern recognition to the stored values, and generating a second recognition signal in response to the occurrence of a predetermined relation between three consecutive daily values.

21. The method of predicting ovulation as defined in claim 20, further comprising the step of displaying a signal indicating very high probability of conception in response to generation of said second recognition signal.

22. The method of predicting ovulation as defined in claim 20, wherein the second of said three consecutive values is less than each of said first and third values by more than a predetermined amount.

23. The method of predicting ovulation as defined in claim 20, further comprising the steps of making daily determinations of the electrical resistivity of the subject's vaginal mucus beginning after the generation of said first recognition signal by applying a second sensor on the subject's cervix for forming analog data signals representing vaginal electrical resistivity, converting said analog data signals to digital data signals, processing said digital data signals over a predetermined time to obtain a digital data signal representing the current daily value of the vaginal electrical resistivity, storing said daily vaginal electrical resistivity values in memory, applying a third algorithm for pattern recognition to the stored values, and generating a third recognition signal in response to the first occurrence of the current daily value being greater than the previous daily value by more than a predetermined significant amount.

24. The method of predicting ovulation as defined in claim 23, further comprising the steps of computing the number of days from the first day of measurement to the day on which said first recognition signal is generated and then calculating the day of ovulation using a regression equation.

25. The method of predicting ovulation as defined in claim 24, further comprising the steps of storing the numbers corresponding to the days on which said first, second, and third recognition signals were generated during a menstrual cycle of a user and storing the number of days in said menstrual cycle, weighting said regressing equation to reflect said stored data, and using said weighted regression equation during the next menstrual cycle to calculate the day of ovulation.

26. The method of predicting ovulation as defined in claim 16, further comprising the steps of making daily determinations of the electrical resistivity of the subject's vaginal mucus beginning after the generation of said first recognition signal by applying a second sensor on the subject's cervix for forming analog data signals representing vaginal electrical resistivity, converting said analog data signals to digital data signals over a predetermined time to obtain a digital data signal representing the current daily value of the vaginal electrical resistivity, storing said daily vaginal electrical resistivity values in memory, applying a third algorithm for pattern recognition to the stored values, and generating a second recognition signal in response to the first occurrence of the current daily value being greater than the previous daily value by more than a predetermined significant amount.

27. The method of predicting ovulation as defined in claim 26, further comprising the step of displaying a signal indicating a low probability of conception one day after the generation of said second recognition signal.

* * * * *